United States Patent [19]

Newlander

[11] Patent Number: 5,908,960
[45] Date of Patent: Jun. 1, 1999

[54] COMPOUNDS

[75] Inventor: Kenneth Allen Newlander, West Chester, Pa.

[73] Assignee: SmithKline Beecham Corporation, Pa.

[21] Appl. No.: 09/067,348

[22] Filed: Apr. 27, 1998

Related U.S. Application Data

[60] Provisional application No. 60/045,808, May 7, 1997.
[51] Int. Cl.$^6$ .................................................. C07C 233/22
[52] U.S. Cl. ........................... 564/177; 435/7.1; 436/501; 436/518; 436/528; 436/531; 530/333
[58] Field of Search .............................. 564/177; 435/7.1; 436/501, 518, 528, 531; 530/333

[56] References Cited

FOREIGN PATENT DOCUMENTS

| WO 92/00091 | 1/1992 | WIPO | ............................ A61K 37/02 |
| WO 92/09300 | 6/1992 | WIPO | ............................ A61K 37/02 |
| WO 94/08051 | 4/1994 | WIPO | ............................ C12Q 1/68 |
| WO 95/30642 | 11/1995 | WIPO | ........................... C07C 205/06 |
| WO 95/32184 | 11/1995 | WIPO | ........................... C07C 277/00 |
| WO 95/35278 | 12/1995 | WIPO | ........................... C07D 207/12 |
| WO 97/08190 | 3/1997 | WIPO | .............................. C07K 1/04 |

OTHER PUBLICATIONS

DeWitt, et al., "'Diversomers': An Approach to Nonpeptide, Nonoligomeric Chemical Diversity", *Proc. Natl. Acad. Sci. USA*, vol. 90, pp. 6909–6913, (1993).
Jung, et al., "Multiple Peptide Synthesis Methods and Their Applications", *Angew. Chem. Int. Ed. Engl.*, vol. 31, pp. 367–383, (1992).
Pavia, et al., "The Generation of Molecular Diversity", *Bioorg. Med. Chem. Lett.*, vol. 3, pp. 387–396, (1993).
Lam, et al., "A New Type of Synthetic Peptide Library for Identifying Ligand–Binding Activity", *Nature*, vol. 354, pp. 82–84, (1991).
Geysen, et al., "Strategies for Epitope Analysis Using Peptide Synthesis", *J. Immunol. Meth.*, vol. 102, pp. 259–274, (1987).
Houghten, et al., "Generation and Use of Synthetic Peptide Combinatorial Libraries for Basic Research and Drug Discovery", *Nature*, vol. 354, pp. 84–86, (1991).
Lebl, et al., "Multiple Release of Equimolar Amounts of Peptides from a Polymeric Carrier Using Orthogonal Linkage–Cleavage Chemistry", *Int. J. Peptide Protein Res.*, vol. 41, pp. 201–203, (1993).
Ellman, et al., "A General and Expedient Method for the Solid–Phase Synthesis of 1,4–Benzodiazepine Derivatives", *Amer. Chem. Soc.*, vol. 114, pp. 10997–10998, (1992).
Furka, et al., "General Method for Rapid Synthesis of Multicomponent Peptide Mixtures", *Int. J. Peptide Protein Res*, vol. 37, pp. 476–487, (1991).
Furka, et al., 14th Intl Congress of Biochemistry, Prague, Jul. 1988.
Wigler, et al., "Complex Synthetic Chemical Libraries Indexed With Molecular Tags", *Proc. Nat. Acad. Sci. USA*, vol. 90, pp. 10922–10926, (1993).

*Primary Examiner*—Brian M. Burn
*Attorney, Agent, or Firm*—Stephen Venetianer; Charles M. Kinzig

[57] ABSTRACT

The present invention relates to libraries of compounds based upon a N-benzyl-N-alkyl-4-alkoxybenzamide, N-benzyl-N-alkyl-4-alkoxyphenylacetamide and N-benzyl-N-alkyl-3-(4-alkoxyphenyl)propionamide template to processes for the preparation of such libraries and their use as a screening tool in biological assays for identifying new chemical leads.

5 Claims, No Drawings

COMPOUNDS

This Application claims benefit of Provision of Application Ser. No. 60/045,808, filed May, 07, 1997

FIELD OF THE INVENTION

This application relates to libraries of compounds based upon a N-benzyl-N-alkyl4-alkoxybenzamide, N-benzyl-N-alkyl-4-alkoxyphenylacetamide and N-benzyl-N-alkyl-3-(4-alkoxyphenyl)propionamide template, to processes for the preparation of such libraries and their use as a screening tool in biological assays for identifying new chemical leads.

BACKGROUND OF THE INVENTION

In the past, new leads for drug discovery have been generated by random cross screening of single synthetic compounds made individually in the laboratory or by screening extracts obtained from natural product sources such as microbial metabolites, marine sponges and plants. A second approach has been rational drug design based on the structure of known biologically active compounds and/or their sites of biological action. This has now been complemented by the powerful techniques of computer-assisted drug design.

There has recently been an explosion in the availablity of new screening targets arising from the output of efforts to sequence the human genome and bacterial genomes. This has led to the development of high throughput screening techniques. Groups of compounds, typically eight, are exposed to a biological target. These groups may be assembled from collections of compounds previously individually prepared and since stored in a compound bank, the assembly being random or guided by the use of "similarity" programs. In addition, there has also been a rapid growth in the deliberate preparation and use of so-called libraries and/or arrays of compounds. Each library contains a large number of compounds which are screened against a biological target such as an enzyme or a receptor. When a biological "hit" is found, the compound responsible for the "hit" is identified. Such compound, or lead, generally exhibits relatively weak activity in the screen but forms the basis for the conduct of a more traditional medicinal chemistry program to enhance activity. The libraries may be prepared using the rapidly developing techniques of combinatorial chemistry or by parallel synthesis (DeWitt et al, Proc Natl Acad Sci, 90, 6909, August 1993; Jung et al, Angew Chem Int Ed Engl, 31:367–83, 1992; Pavia et al., Bioorg Med Chem Lett, 3:387–1993).

The first libraries were composed of small polypeptides, with some libraries containing up to 10,000 members. Such libraries could be made by adapting the techniques developed for the synthesis of single polypeptides (see, for instance, Lam et al, Nature, 354: 82, 1991 and WO 92/00091; Geysen et al, J Immunol Meth, 102: 259, 1987; Houghten et al, Nature, 354: 84, 1991 and WO 92/09300 and Lebi et al, Int J Pept Prot Res, 41, 201, 1993). The chemistry involved, forming an amide bond, is relatively straightforward and automated peptide synthesisers can be employed to reduce the manual effort involved. However, small polypeptides do not provide ideal leads for drug discovery. Peptides are not generally useful as therapeutic agents and there exists no rational way of translating a peptide into a therapeutically useful small molecule (peptidomimetic). A similar approach has also been used with nucleotides, taking advantage of the progress made in automated nucleotide synthesis, and with oligomers.

Attention has therefore turned to preparing libraries of small non-peptide molecules based upon a common template or core structure [see for instance Ellman and Bunin, J Amer Chem Soc, 114:10997, 1992 (benzodiazepine template), WO 95/32184 (oxazolone and aminidine template), WO 95/30642 (dihydrobenzopyran template) and WO 95/35278 (pyrrolidine template)]. The template will have a number of functional sites, for instance three, each of which can be reacted, in a step-wise fashion, with a number of different reagents, for instance five, to introduce 5×5×5 different combinations of substituents, giving a library containing 125 components. The library will normally contain all or substantially all possible permutations of the substituents. The template may be a so-called 'biased' template, for instance incorporating a known pharmacophore such as a benzodiazepine ring or a so-called 'unbiased' template, the choice of which is influenced more by chemical than biological considerations. Unbiased templates are considered to offer the greater potential for generating entirely new leads.

The real challenge in creating a small molecule library which is useful as a screening tool is to provide a diverse range of substituents comprising a wide range and variety of structural units which allow the library as a whole to explore as fully as possible the active site of a receptor or an enzyme in an assay by having the potential for a wide range of interactions such as hydrogen bonds, salt bridges, π-complexation, hydrophobic effects etc. The actual substituents are selected by considering their physico-chemical properties such as, for example, electronic, ionic, lipophilic and steric properties in order that the library contains maximum structural diversity. For example, if a core structure is to have a $C_{1-6}$ alkyl substituent at a particular position, a typical library may have component compounds in which that substituent is methyl and t-butyl. An adamantyl group provides a good example of a large, bulky hydrophobic group. Substituents on an aromatic ring may be varied according to well established principles of medicinal chemistry, e.g., as reflected in the Topliss and Craig diagrams. Suitable diverse heteroaryl groups may be chosen according to well-known medicinal chemistry principles. For instance, a pyridinyl group may be selected if a basic group is desired. In addition, computer programs have now been developed to assist in this process, for instance SYBYL molecular diversity manager (Tripos Inc, Mo, USA). It is also useful to avoid mass redundancies when selecting suitable substituents, to aid identification of different library members by mass spectroscopy. Tables have been devised to assist in this task (PCT/EP96/03731, SmithKline Beecham).

For maximum synthetic efficiency in creating a library, the introduction of different substituents at each functional site should be accomplished as a single step, using a mixture of reagents, one for each different substituent. A diverse range of substituents can however translate into a diverse range of reactivities for the reagents. It is often more convenient to adopt the so-called 'split and mix' approach whereby the evolving library is split into a series of parallel aliquots, each containing the same mixture. Each aliquot is then reacted with a single but different reagent, to introduce a further variant, and the new sub-libraries can then be recombined before splitting again, for a further synthetic cycle (Furka et al, 14th Intl Congress of Biochemistry, Prague, July 1988; Furka et al, Int J Peptide Protein Res, 37: 487, 1991). Such an approach is of assistance in coping with different reactivities of diverse reagents and also in deconvoluting a library, once a hit is found. The progress of reactions may be monitored using various techniques, for instance the disappearance of a functional group such as an amine. Single bead mass spectroscopy allows the possibility of selectively sampling and analyzing large numbers of compounds, enabling this technique to be used to monitor and/or analyze libraries. Solid phase NMR, in particular so-called 'magic angle' NMR, can also be usefully applied.

A complementary approach to creating a library of compounds is to use the parallel synthesis method, whereby the compounds comprising the library are prepared separately and in parallel. Usually, the various reaction steps are not monitored and little or no effort is made to purify or isolate intermediate compounds (DeWitt et al, Proc Nat Acad Sci USA, 90:6909–13, 1993). The chemistry may be carried out in the solution phase or using solid phase supports. This allows for a greater rate of synthesis, although at the possible expense of incomplete reactions. Compounds may be screened individually or they may be grouped together, for instance if there is a limited supply of screening target. Either way, deconvolution, once a "hit" is found, is then assisted by the existence of individual compounds. This approach is becoming increasingly automated and is attractive for the preparation of a small number of compounds. For larger libraries, the combinatorial approach becomes increasingly more efficient, as far fewer reactions have to be carried out.

The screens in which the libraries are assayed tend to be based on enzymes or receptors. These are becoming increasingly automated, giving them a high throughput and making the use of libraries more attractive. Furthermore, once created, libraries can become a screening resource which can be used many times over, both for existing screens and, held in reserve, for new screens as they are developed.

SUMMARY OF THE INVENTION

An object of the present invention is to provide a library of compounds based on N-benzyl-N-alkyl-4-alkoxybenzamide, N-benzyl-N-alkyl-4-alkoxyphenylacetamide and N-benzyl-N-alkyl-3-(4-alkoxyphenyl)propionamide templates and sub-libraries thereof. A further object of the present invention is to provide processes for the preparation of such libraries. Yet another object of the present invention is to provide processes for the use of such libraries as screening tools in biological assays for identifying new chemical leads.

DETAILED DESCRIPTION OF THE INVENTION

The present invention provides for a library comprising 1,215 different compounds of Formula I:

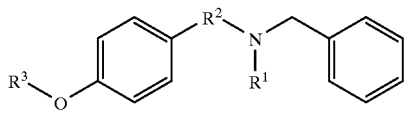

Formula I wherein:
$R^1$ is pentyl, allyl, phenethyl, 3-trifluoromethylbenzyl, 4-fluorophenethyl, 4-bromophenethyl, 3,3-diphenylpropyl, 4-methoxyphenethyl, 2-isopropyloxyethy, carboxyethyl, (+/−)-2-tetrahydofuranylmethyl, 3-chlorobenzyl, 2-(1-piperidinyl)ethyl, 5-cyanopentyl, cyclohexyl, 2-dimethylaminoethyl, 2-(2-pyridinyl)ethyl, 2,6-dichlorophenethyl, 2,5-difluorophenethyl, 1-(+/−)-1,2, 3,4-tetrahydonaphthyl, 4-t-butylcyclohexyl, 2-thiophenylmethyl, 2,2,2-trifluoroethyl, 3,4-dimethoxyphenethyl, 3-(1-imidazoyl)propyl, 2-(4-morpholino)ethyl, or 5-aminopentyl;

$R^2$ is —CO—, —CH$_2$CO— or —CH$_2$CH$_2$CO—;

$R^3$ is 2-dimethylaminoethyl, 3-dimethylaminopropyl, (+/−)-1-methyl-3-piperidinylmethyl, 4pyridinylmethyl, 3-pyridinylmethyl, 6-dimethylaminohexyl, 2-(methylphenylamino)ethyl, 2-(benzylmethylamino)ethyl, 2-pyridinylmethyl, 3-(4-pyridinyl)propyl, hydro, 5-diethylaminopentyl, 3-(4-pyridinyl)propyl, 4-dimethylaminophenethy or 2-(2-oxo-3-oxazolinyl)ethyl.

Such a library is useful in screening for new chemical leads for drug discovery.

Suitably, the library is a combinatorial library, that is, a library prepared using a combinatorial chemistry approach.

The term "library" as used hereinafter refers to a collection of individual compounds which have a common core structure or template which has a discrete number of independently variable substituents, each of which can have one of a defined range of values. Preferably, the library is designed so that, for the range of values selected for each of the independently variable substituents, compounds containing all possible permutations of these substituents will be present in the library. Thus, if a template contains three independently variable substituents, X, Y and Z, and if X is one of m different chemical moieties, Y is one of n different chemical moieties and Z is one of p different chemical moieties (in which m, n and p are integers which define the size of the library, and which range between 1 to 1000; preferably between 1 to 100; more preferably between 1 to 20), then the library would contain m×n×p different chemical compounds and all possible combinations of X, Y and Z would be present on the template within the library. This may be regarded as an "ideal" or complete library. The term "library" is also used to refer to a collection of compounds in which substantially all of the members of the 'ideal' or complete set of compounds are present, for instance at least 80%, preferably 90%, more preferably 95%. It will be appreciated that, in some instances, a certain number of the individual compound members of a library might not synthesized, for instance a particular intermediate may show low reactivity towards a specific reagent as a consequence of steric hindrance or electronic factors. In addition, a statistical analysis of a library prepared using the "split and mix" technique shows that not all the compounds theoretically preparable will in reality be prepared. A library may be composed of a series of sub-libraries, each having the same common core and, for instance, all permutations of X and Y and each sub-library having only one value of Y. For the purposes of screening, it may be more convenient to keep the sub-libraries separate, rather than combine them.

A typical library will contain between 2 to 10,000 or more compounds, preferably 10 to 1,000 compounds, and more preferably 10 to 500 compounds. A typical sub-library may comprise up to 200 members.

Such libraries are suitably prepared by the methods of combinatorial chemistry or by parallel synthesis.

It will be readily appreciated that smaller sub-libraries of the main libraries may also be prepared and these are of use in deconvoluting a main library. Compounds of a library may be bound to a solid phase support such as a resin, used to facilitate the synthesis thereof, and this is generally referred to as a 'solid phase' library, in particular a 'resin-bound' library. Compounds of a library which have been cleaved from a solid phase support are generally referred to as a 'soluble' library. The present invention encompasses all such libraries and sub-libraries. Suitable sub-libraries include those given in which either $R^1$ or $R^2$ have the full range of values while the other R group has a single, fixed value.

Compounds for inclusion in libraries according to the present invention may be made by the combinatorial approach. Alternatively, such compounds may be made individually, either by a conventional synthesis or by the parallel synthesis approach, using manual or automated techniques.

The compounds of Formula I are prepared by solid phase organic synthesis. Suitable solid phase supports include resins which are well known in the art and include includes beads, pellets, disks, capillaries, hollow fibers, needles, solid fibers, cellulose beads, pore-glass beads, silica gels, poly-styrene beads optionally cross-linked with divinylbenzene, grafted co-poly beads, poly-acrylamide beads, latex beads, dimethylacrylamide beads optionally cross-linked with N,N-bis-acryloyl ethylene diamine, POLY-HIPE™, TENTAGEL™, etc. Both smaller (for instance about 30 to 80 μm) and larger beads (for instance about 200 to 300 μm) are available from commercial suppliers. the latter being prefered for single bead screening.

The template is synthesized from a 4-(hydroxymethyl) phenyl-2-dimethylsilyl)propionamidomethylphenyl resin. The hydroxymethylphenyl group is first transformed to a resin bound benzylbromide, separated into 27 reaction vessels and alkylated with the 27 amines derived from R1. The 27 reactions are next combined, mixed, then separated into three reaction vessels. The secondary amines are next acylated with three phenol-acids derived from R2 [ie. 4-hydroxybenzoic acid, 4-hydroxyphenylacetic acid and 3-(4-hydroxyphenyl)propionic acid], coupled using standard coupling methods. The three reactions are then combined and mixed again. Any acylated phenol is then hydrolyzed by treatment with base, separated into 14 reaction vessels and coupled with the 14 alcohols derived from R3 via the Mitsunobu reaction. The final product of Formula I is released from the resin by treatment with trifluoroacetic acid or any method known to cleave aryl silicon bonds. A representative synthesis is given in Scheme 1 below. As used herein in Scheme 1, the term "polymer" is a polystyrene polymer.

It will be appreciated that reactive functional groups in the alkyl and acyl substituents $R^2$ and $R^3$ may require temporary protecting groups during the synthesis. Ideally, these protecting groups are either selectively removable before cleavage from the resin or are removed concomittantly with cleavage of the compound from the resin. For example, primary and secondary amino groups can be protected as their t-Boc derivatives, alcohols or phenols as their t-butyl ether derivatives and carboxylic acids as their t-butyl ester derivatives.

Scheme 1

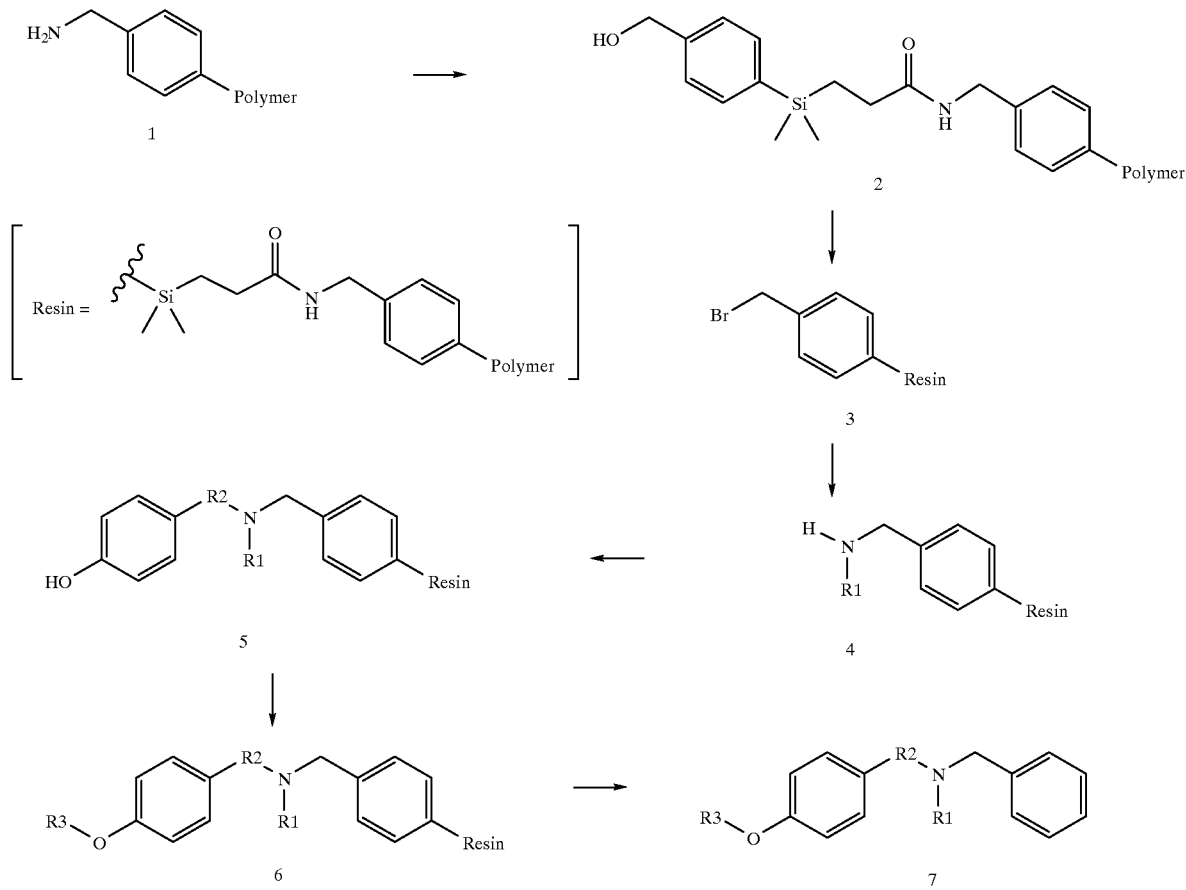

In the following synthetic examples, temperature is in degrees Celsius (°C.). Unless otherwise indicated, all of the starting materials were obtained from commecial sources. Without further elaboration, it is believed that one skilled in the art can, using the description provided in this specification, utilize the present invention to its fullest extent. These examples are given to illustrate the invention, not to limit its scope. Reference is made to the claims for what is reserved to the inventors hereunder.

EXAMPLE 1

Preparation of Aminomethyl Polystyrene 1% DVB. (1-Scheme 1)

To chloromethylated polystyrene 1% DVB (25 g, Polymer Labs, 2.0 mmol/g, avg. dia. 290 u) in a silanized 500 mL round bottom flasked were added potassium di-t-butyl iminodicarboxylate (25 g, 80 mmol) and dry DMF (200 mL). The reaction mixture was purged with argon and stirred by rotation, under argon, on a rotovap at 60 ° C. for 24 h. The reaction was then cooled, filtered and washed successively with DMF (×2), (1:1) DMF, $H_2O$ (×2), methanol (×2), air dried for 16 h then dried under vacuum for 24 h. Analysis % N 1.96 (95% of theoretical); MAS-NMR (500 mHz, $CDCl_3$) disappearance of the peaks at d 4.38 and 4.50 ppm (chloromethyl polystyrene) and formation of a new methylene peak at d 4.62 ppm and a t-butyl peak at d 1.38 ppm.

The above resin was treated with a solution of 90% trifluoroacetic acid in $CH_2Cl_2$ (200 mL) for 1 h at room temperature, filtered, washed with $CH_2Cl_2$ (×2), neutralized with a solution of 10% diisopropylethylamine (DIEA) in $CH_2Cl_2$ (200 mL) for 15 min., washed with $CH_2Cl_2$ (×2), then methanol (×4). The resin was air-dried for 16 h then dried under vacuum for 24 h. (23.45 g) Analysis % N 3.01, calculated substitution 2.15 mmol/g; MAS-NMR (500 mHz, $CDCl_3$) d 3.76 and 3.63 ppm.

EXAMPLE 2

Preparation of 3-[4-(hydoxymethyl) phenyldimethylsilyl]propionamidomethyl polystyrene 1% DVB. (2-Scheme 1)

3-[4-(hydroxymethyl)phenyldimethylsilyl]propionic acid (14.9 g, 63 mmol) (reference patent or manuscript in preparation), 1-hydroxybenzotriazole (HOBt) (16.9 g, 125 mmol) and dicyclohexylcarbodiimide (DCC) (14.4 g, 70 mmol) were added to a slurry of aminomethylated polystyrene 1% DVB (25.0 g, 2.15 mmolg, 53 mmol) and DMF (200 mL). The slurry was shaken for 16 h, filtered, washed with DMF (×2), (1:1) $CHCl_3$, MeOH (×2), $CH_2Cl_2$ (×2), MeOH (×4) and dried under vacuum for 24 h. A Kaiser test (E. Kaiser, R. L. Colescott, C. D. Bossinger and P. I. Cook, *Anal. Biochem.* 34, 595–598, 1970) of the resulting resin was negative. Analysis % N 1.18, calculated substitution 1.30 mmol/g; MAS-NMR (500 mHz, $CDCl_3$) d (7.44, 2H), (7.29, 2H), (4.56, 2H), (4.20, 2H), (2.06, 2H), (1.06, 2H), (0.26, 6H).

EXAMPLE 3

Preparation of 3-[4-(bromomethyl) phenyldimethylsilyl]propionamidomethyl polystyrene 1% DVB. (3-Scheme 1)

To a suspension of resin 2-Scheme 1 (6.0 g, 7.8 mmol) in dry THF (80 mL) in a shaker vessel were added $CBr_4$ (5.4 g, 16.3 mmol) followed by triphenylphosphine (4.3 g, 16.4 mmol). The reaction was shaken for 24 h. (A thick white precipatate formed.) The resin was washed with THF (×3), EtOH (×2), $CH_2Cl_2$ (×2) then dried under vacuum for 24 h. (7.7 g) Analysis % N 1.41, % Br 8.36, calculated substitution 1.05 mmol/g; MAS-NMR (500 mHz, $CDCl_3$) disappearance of the peak at d 4.56 and formation of a new methylene peak at d 4.24 ppm.

EXAMPLE 4

General Preparation of Secondary-amines. (4-Scheme 1)

To a suspension of resin 3-Scheme 1 (300 mg, 0.32 mmol) in dry DMF (8 mL), in a shaker vessel were added the amine derived from R1 (3.2 mmol, 10 mol equiv.) and triethylamine (448 uL, 3.2 mmol). The reaction was shaken for 24 h, filtered and washed with DMF (×2), MeOH (×2), (1: 1) $CHCl_3$, MeOH (×2), MeOH (×2) then dried under vacuum.

EXAMPLE 5

General Proceedure for the Acylation of the Secondary Amines. (5- Scheme 1)

To a suspension of resin 4-Scheme 1 (3.0 g, ~2.9 mmol) in DMF (30 mL) in a shaker vessel were added the phenolic-acid derived from R2 [ie. 4-hydroxybenzoic acid, 4-hydroxyphenylacetic acid or 3-(4-hydroxyphenyl) propionic acid] (3.5 mmol, 1.2 equiv.), N-methylmorpholine (2.0 mL, 18 mmol), HOBt (0.95 g, 7 mmol) and HBTU (1.33 g, 3.5 mmol). The reaction was shaken for 24 h, washed with DMF (×2), (1:1) $CHCl_3$, methanol (×2), $CH_2Cl_2$ (×2) and methanol (×2).

All of the above reactions after coupling were saponified with a solution of (1:1) aq. 1N NaOH, DMF (30 mL) with shaking at room temperature for 16 h then washed with (1:1) DMF, $H_2O$ (×2), a solution of HOAc (1 mL, 17 mmol) in (1:1) DMF, H2O (30 mL), (1:1) DMF, $H_2O$ (×2), DMF (×2), methanol (×2) and THF (×2).

EXAMPLE 6

General Proceedure for Doing the Mitsunobu Reaction. Resin 6-Scheme 1

To a suspension of resin 5-Scheme 1 (300 mg, ~0.36 mmol) in dry THF (8 mL) under an atmosphere of Ar were added the alcohol derived from R3 (1.8 mmol, 5 equiv.), triphenylphosphine (0.48 g, 1.8 mmol), followed by diisopropyl azodicarboxylate (DIAD) (0.36 mL, 1.8 mmol). The reaction was shaken for 4 h then washed with THF (×2). The reaction was repeated four times then thoroughly washed with THF (×2), methanol (×2), $CH_2Cl_2$ (×2), hexane a nd dried under vacuum.

EXAMPLE 7

General Proceedure for Doing the TFA Vapor Cleavage Reaction. Compound 7-Scheme 1

Resin 6-Scheme 1 (From a single bead to a bulk sample) was exposed to TFA vapor (by placing the resin in a filter funnel or open vial, within a closed container containing a layer of TFA on the bottom) at room temperature for 72 h. The resin after drying under vacuum and extraction with methanol, filtration and evaporation gives compound 7-Scheme 1.

The "split and mix" technique referred to previously may conveniently be used to more efficiently conduct the synthesis of the final library and also to provide intermediate sub-libraries to assist the deconvolution of a library, once a "hit" has been made in a biological assay. It will be understood that by using this approach, each bead will have bound to it a unique compound member of the library.

Accordingly, in a further aspect, the present invention provides a method for synthesizing a combinatorial library of different compounds, comprising the steps of:

(a) attaching a compound of Formula II:

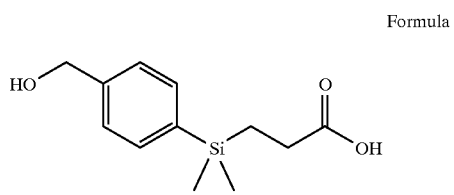

Formula II to resin beads selected from the group consisting of benzydrylamino or aminomethylated polystyrene;

(b) transformation the above resin to the corresponding resin bound benzylbromide.

(c) splitting the resin beads into 27 first aliquots;

(d) reacting each of said first 27 aliquots with a different amine selected from a group of amines consisting of pentylamine, allylamine, phenethylamine, 3-trifluoromethylbenzylamine, 4-fluorophenethylamine, 4-bromophenethylamine, 3,3-diphenylpropylamine, 4-methoxyphenethylamine, 2-isopropyloxyethylamine, t-butyl 3aminopropanoiate, (+/-)-2-tetrahydofuranylmethylamine, 3-chlorobenzylamine, 2-(1-piperidinyl)ethylamine, 5-cyanopentylamine, cyclohexylamine, 2-dimethylaminoethylamine, 2-(2-pyridinyl) ethylamine, 2,6-dichlorophenethylamine, 2,5-difluorophenethylamine, 1-(+/-)-1,2,3,4-tetrahydonaphthylamine, 4-t-butylcyclohexylamine, 2-thiophenylmethylamine, 2,2,2-trifluoroethylamine, 3,4-dimethoxyphenethylamine, 3-(1-imidazoyl) propylamine, 2-(4-morpholino)ethylamine, and mono t-butoxycarbonyl-1,5-diaminopentane;

(e) mixing together the 27 different first reaction products to form a mixture;

(f) splitting said first mixture into 3 second aliquots;

(g) coupling each of said 3 second aliquots with a different carboxylic acid selected from a group of carboxylic acids consisting of 4-hydroxybenzoic acid, 4-hydroxyphenylacetic acid and 3-(4-hydroxyphenyl) propionic acid to provide 3 second reaction products;

(h) mixing together the 3 different second reaction products to form a mixture;

(i) saponifying any acylated phenolic esters.

(j) splitting said second mixture into 14 third aliquots;

(k) coupling each of said 14 third aliquots by the Mitsunobu reaction with a different alcohol selected from a group of alcohols consisting of 2-dimethylaminoethanol, 3-dimethylaminopropanol, (+/-)-1-methyl-3-piperidinylmethanol, 4-pyridinylmethanol, 3-pyridinylmethanol, 6-dimethylaminohexanol, 2-(methylphenylamino) ethanol, 2-(benzylmethylamino)ethanol, 2-pyridinylmethanol, 3-(4-pyridinyl)propanol, 5-diethylaminopentanol, 3-(4-pyridinyl)propanol, 4-dimethylaminophenylethanol or 2-(2-oxo-3-oxazolinyl)ethanol to provide 14 third reaction products; (1) optionally, and if so desired, cleaving at least a portion of the third reaction products with trifluoroacetic acid or any known reagent that cleaves aryl-silyl bonds to provide the library in soluble form.

It will be understood that for an aliquot when $R^3$ is hydrogen, step (k) of the process will not be performed.

Formula II may be prepared by the process described in U.S. provisional application 60/017,955 filed May 20, 1996.

Libraries in which the members thereof are bound to a solid phase support are particularly useful as intermediates in the preparation of final libraries. Accordingly, in a further aspect, the present invention provides for a library comprising up to 81 different compounds of Formula III:

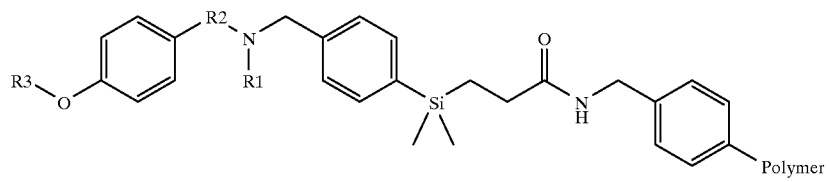

Formula III in which $R^3$ is as hereinbefore defined.

Single beads having a single compound may be prepared by parallel synthesis or the split and mix techniques hereinbefore described. In a further aspect, the present invention provides for a resin bead having a single compound of Formula I. Such beads are preferred for screening purposes. Useful libraries of the present invention are those consisting of resin beads in which each resin bead has a single compound of Formula I.

Libraries of the present invention are useful as screening tools, for the identification of compounds with biological activity. Accordingly, in a further aspect, the present invention provides for the use of a library as hereinbefore defined in identifying compounds with biological activity.

Conventionally, libraries have been screened as solutions in aqueous dimethyl sulphoxide. Polymer bound libraries are first cleaved to create soluble libraries. Small (microlitre) volumes can then be reproducibly and accurately measured out for use in each assay, as needed. The solutions can be stored frozen at low temperature (-20° C.), to prolong the useful life thereof.

After a "hit" is found in a soluble library, the library is deconvoluted to identify the member(s) thereof responsible for the "hit", according to principles well-known to those skilled in the art, for instance using an iterative or a scanning approach.

Using an iterative approach, sub-libraries of decreasing complexity are screened individually, to narrow down the field of search. These may have been created during the original synthesis of the library, with a portion being set aside. Alternatively, a first sub-library may be prepared by repeating all but the final step of the preparation of the library, so that this sub-library contains all the possible variations in substituents at all but one position. This sub-library is then split into a series of aliquots, one for each variation in the remaining substituent. Each aliquot is then treated with a different reagent which will introduce each of the variations of the final substituent, individually. This will create a series of parallel sub-libraries, each of which will have a single value for the final substituent. These can then be screened, to identify which of the values of the final substituent is responsible for the 'hit'. The iteration may then be continued for the other substituents, starting with a sub-library containing all but the final two substituents. This sub-library is then divided into a series of aliquots for introducing individually each of the values of the penultimate substituent. Each of the aliquots is then reacted with a reagent to introduce the value of the ultimate substituent which was found to give a 'hit', thereby creating a series of parallel sub-libraries. These can then be screened to identify which combination(s) of the ultimate and penultimate substituents give a 'hit'. Ultimately, it will become necessary to prepare the individual members of a sub-library, to identify the specific compound. The parallel synthesis approach may be of use in this process. If a template has three variables X, Y and Z, each of which can have a, b and c values, to give a library with a×b×c members, it can be deconvoluted by the iterative approach with a+b+c syntheses.

Using the scanning approach, a series of sub-libraries is created, each containing all the variations in substituents at all but one of the positions. Each sub-library is then divided into a series of aliquots so that each of the values of the remaining substituent may then be introduced individually, to create a set of parallel sub-libraries. Each of these may then be screened, to identify which of the values of each of the variables is responsible for activity.

Deconvolution of combinatorial libraries and sub-libraries may also be assisted by applying analytical techniques conventionally used for resolving mixtures of compounds. In particular, consecutive HPLC, using a series of different columns and different eluants, in combination with mass spectrometry may allow identification of individual members of a library.

For resin libraries, "hit" identification may also be effected by encoding for each of the members of a library with a unique marker, for instance the binary tagging system described by Wigler M et al, Proc Nat Acad Sci USA, 1993, 90, 10922–10926 and in WO 94/08051.

In addition, the compounds of a library may be screened whilst still attached to a resin, for instance beads. In particular, single bead screening may be used. Accordingly, in a further aspect, the present invention provides for a library consisting of n compounds of Formula IV wherein each resin bead has substantially a single compound, the beads being disposed in an array of single beads, the size of the array being choosen so that statistically there is at least a 90% probability; preferably at least a 95% probabilty that the array will contain a representative of each member of the library present. Suitably, for a 95% probability, 3n beads are arrayed.

Each member may remain bound to the bead or the member may be chemically cleaved from the resin using known cleavage methods and then screened. Generally, screening involves arranging each of the individual beads into a single well of a multiple well microtiter plate. Then, in each well, the compound is released from the bead using known cleavage methods, after which a receptor binding assay or any other known bioassay (for example, one which determines inhibition of a target enzyme) is performed. If a bioactive compound member of the library is found as a result of the screening procedure, identification of that compound is made using traditional methods of structure elucidation, particularly, mass spectrometry and nuclear magnetic resonance spectroscopy. The bead may be subjected to conditions which effect either total or partial cleavage of the library member from the bead. Partial cleavage, sometimes referred to as "shaving" allows the bead to be reused for further assays or, if a hit is given, identification of the compound.

It is expected that, in general, the hits thus obtained will not have sufficient biological activity to be of therapeutic interest. However, chemical elaboration of such hits is expected to provide a compound suitable for development as a therapeutic agent. Further compounds may be prepared as a combinatorial library or an arrays of compounds, by parallel synthesis, as well as more conventional single compound synthesis.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A combinatorial library comprising up to 1,215 different compounds of Formula I:

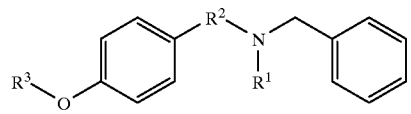

Formula I wherein:

$R^1$ is pentyl, allyl, phenethyl, 3-trifluoromethylbenzyl, 4-fluorophenethyl, 4-bromophenethyl, 3,3-diphenylpropyl, 4-methoxyphenethyl, 2-isopropyloxyethyl, carboxyethyl, (+/−)-2-tetrahydofuranylmethyl, 3-chlorobenzyl, 2-(1-piperidinyl)ethyl, 5-cyanopentyl, cyclohexyl, 2-dimethylaminoethyl, 2-(2-pyridinyl)ethyl, 2,6-dichlorophenethyl, 2,5-difluorophenethyl, 1-(+/−)-1,2,3,4-tetrahydonaphthyl, 4-t-butylcyclohexyl, 2-thiophenylmethyl, 2,2,2-trifluoroethyl, 3,4-dimethoxyphenethyl, 3-(1-imidazoyl)propyl, 2-(4-morpholino)ethyl, or 5aminopentyl;

$R^2$ is —CO—, —CH$_2$CO— or —CH$_2$CH$_2$CO—;

$R^3$ is 2-dimethylaminoethyl, 3-dimethylaminopropyl, (+/−)-1-methyl-3-piperidinylmethyl, 4-pyridinylmethyl, 3-pyridinylmethyl, 6-dimethylaminohexyl, 2-(methylphenylamino)ethyl, 2-(benzylmethylamino)ethyl, 2-pyridinylmethyl, 3-(4-pyridinyl)propyl, hydro, 5-diethylaminopentyl, 3-(4-pyridinyl)propyl, 4-dimethylaminophenethyl or 2-(2-oxo-3-oxazolinyl)ethyl.

2. A process for making a combinatorial library comprising the steps of:

(a) attaching a compound of Formula II:

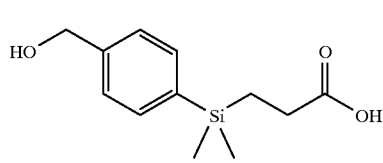

Formula II to resin beads selected from the group consisting of benzydrylamino or aminomethylated polystyrene;
(b) transforming the above resin to the corresponding resin bound benzylbromide;
(c) splitting the resin beads into 27 first aliquots;
(d) reacting each of said first 27 aliquots with a different amine selected from a group of amines consisting of pentylamine, allylamine, phenethylamine, 3-trifluoromethylbenzylamine, 4-fluorophenethylamine, 4-bromophenethylamine, 3,3-diphenylpropylamine, 4-methoxyphenethylamine, 2-isopropyloxyethylamine, t-butyl 3-aminopropanoiate, (+/-)-2-tetrahydofuranylmethylamine, 3-chlorobenzylamine, 2-(1-piperidinyl)ethylamine, 5-cyanopentylamine, cyclohexylamine, 2-dimethylaminoethylamine, 2-(2-pyridinyl)ethylamine, 2,6-dichlorophenethylamine, 2,5-difluorophenethylamine, 1-(+/-)- 1,2,3,4-tetrahydonaphthylamine, 4-t-butylcyclohexylamine, 2-thiophenylmethylamine, 2,2,2-trifluoroethylamine, 3,4-dimethoxyphenethylamine, 3-(1-imidazoyl) propylamine, 2-(4-morpholino)ethylamine, and mono t-butoxycarbonyl-1,5-diaminopentane;
(e) mixing together the 27 different first reaction products to form a mixture;
(f) splitting said first mixture into 3 second aliquots;
(g) coupling each of said 3 second aliquots with a different carboxylic acid selected from a group of carboxylic acids consisting of 4-hydroxybenzoic acid, 4-hydroxyphenylacetic acid and 3-(4-hydroxyphenyl) propionic acid to provide 3 second reaction products;

(h) mixing together the 3 different second reaction products to form a mixture;
(i) saponifying any acylated phenolic esters,
(j) splitting said second mixture into 14 third aliquots;
(k) coupling each of said 14 third aliquots by the Mitsunobu reaction with a different alcohol selected from a group of alcohols consisting of 2-dimethylaminoethanol, 3-dimethylaminopropanol, (+/-)-1-methyl-3-piperidinylmethanol, 4-pyridinylmethanol, 3-pyridinylmethanol, 6-dimethylaminohexanol, 2-(methylphenylamino) ethanol, 2-(benzylmethylamino)ethanol, 2-pyridinylmethanol, 3-(4-pyridinyl)propanol, 5diethylaminopentanol, 3-(4-pyridinyl)propanol, 4-dimethylaminophenylethanol or 2-(2-oxo3-oxazolinyl)ethanol to provide 14 third reaction products.

3. The process according claim 2 further comprising the step of:
(j) treating the third reaction products with trifluoroacetic acid or any known reagent that cleaves aryl-silicon bonds to provide a soluble library.

4. A method of identifying a compound having one or more desired characteristics comprising synthesizing a library based on a compound of Formula I:

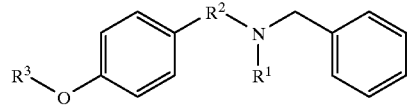

Formula I and testing the compounds of the library in one or more assays which identify compounds having the desired characteristics.

5. A combinatorial library of formula I prepared by the process of claim 2.

* * * * *